(12) United States Patent
Colabella et al.

(10) Patent No.: US 10,503,870 B2
(45) Date of Patent: Dec. 10, 2019

(54) PAYMENT BRIDGE

(71) Applicant: Retriever Enterprises, LLC, Valhalla, NY (US)

(72) Inventors: Dominick Colabella, Ridgefield, CT (US); Michael Peluso, Southbury, CT (US)

(73) Assignee: Retriever Enterprises, LLC, Valhalla, NY (US)

( * ) Notice: Subject to any disclaimer, the term of this patent is extended or adjusted under 35 U.S.C. 154(b) by 742 days.

(21) Appl. No.: 15/131,617

(22) Filed: Apr. 18, 2016

(65) Prior Publication Data

US 2017/0300642 A1  Oct. 19, 2017

(51) Int. Cl.
*G06Q 20/00* (2012.01)
*G06F 19/00* (2018.01)

(52) U.S. Cl.
CPC .................... *G06F 19/328* (2013.01)

(58) Field of Classification Search
CPC ............................ G06F 19/328; G06Q 20/409
See application file for complete search history.

(56) References Cited

U.S. PATENT DOCUMENTS

| | | | | |
|---|---|---|---|---|
| 6,868,399 B1 * | 3/2005 | Short | ..................... | G06Q 20/14 705/34 |
| 7,945,458 B1 * | 5/2011 | Jackson | ................. | G06Q 10/10 705/2 |
| 9,626,512 B1 * | 4/2017 | Brandwine | ............. | G06F 21/57 |
| 2005/0247777 A1 | 11/2005 | Pitroda | | |
| 2006/0217996 A1 * | 9/2006 | Graves | ................. | G06Q 20/105 705/41 |

(Continued)

OTHER PUBLICATIONS

Authorized Officer: Blaine R. Copenheaver, "International Search Report", issued in counterpart PCT application No. PCT/US2016/028106, dated Jul. 15, 2016, Publisher: PCT, 3 pp.

*Primary Examiner* — Elda G Milef
*Assistant Examiner* — Scott C Anderson
(74) *Attorney, Agent, or Firm* — Kaplan Breyer Schwarz, LLP (57) ABSTRACT

The invention is direct to a payment bridge system for a service provider and in particular a health care provider like a doctor or dentist. A practice management software is installed on the service provider's computer system for managing the service provider's business including managing patient or customer data, issuing invoices and handling payments. The system has a secure gateway network connecting with a secure network provider and a credit card processing system, connected to the secure network provider. A payment bridge installed on the service provider's computer system communicates with the practice management software and the secure gateway network to accept payments by credit card for invoices generated by the practice management system which are securely transmitted through the secure gateway network to the credit card processing system for approval and processing and updating the practice management software to reflect payment by credit card when the charge is accepted by the credit card processing system. All credit card data is encrypted prior to transmission to the credit card processor and no unencrypted credit card data is stored at the service provider's location.

18 Claims, 5 Drawing Sheets

(56) References Cited

U.S. PATENT DOCUMENTS

| | | | | |
|---|---|---|---|---|
| 2006/0224470 | A1* | 10/2006 | Garcia Ruano | G06Q 20/04 705/26.1 |
| 2007/0185803 | A1* | 8/2007 | Harrison | G06F 19/328 705/36 T |
| 2007/0194108 | A1* | 8/2007 | Kalappa | G06Q 40/00 235/381 |
| 2007/0214093 | A1* | 9/2007 | Colella | G06Q 20/04 705/67 |
| 2007/0248225 | A1* | 10/2007 | Fluhrer | H04L 63/0428 380/30 |
| 2009/0019552 | A1* | 1/2009 | McLaughlin | G06Q 30/0203 726/27 |
| 2009/0055259 | A1* | 2/2009 | Lavoice | E05B 19/24 705/14.4 |
| 2011/0282688 | A1* | 11/2011 | Raggousis | G06Q 50/24 705/3 |
| 2013/0117035 | A1 | 5/2013 | Tierney et al. | |
| 2014/0095194 | A1 | 4/2014 | Mahaffey et al. | |
| 2014/0201084 | A1* | 7/2014 | Dagenais | G06Q 20/40 705/64 |

\* cited by examiner

Transactional Flow of Credit Card Information

FIG. 3

Card Data Flow Diagram

PAYMENT BRIDGE

BACKGROUND OF THE INVENTION

The invention is generally directed to a Payment Bridge utilized between a medical or dental practice management software system and a credit card payment processor where there is a desire for existing or future bills to be paid by credit card. Historically, healthcare providers were disposed against accepting credit card transactions as terms of payment. Typically, co-payments and other payments were funded via cash or personal checks. However, this related to several problems associated with the use of credit cards for payments in this area. First, there was a transactional cost associated with the use of credit cards not present when either cash or checks were utilized. Second, there was a risk that a user would disavow or cancel the charge, which would create a deficiency in payment and substantially increase the administrative burden on the medical office for and following charge. Of course, there are problems also associated with the use of checks in that they take several days to clear, preventing the medical or dental office from immediately utilizing the payment and the risk of the check being dishonored either because there are insufficient funds or because the check writer has stopped payment on the check prior to its clearance.

As a result of the widespread growth and use of credit and debit cards over the past several decades there has been increased pressure by patients to allow for the payment through credit cards. This pressure has caused medical and dental offices to begin accepting credit cards, but to generally rely on the credit card capabilities of their practice management software vendor, which is generally relatively expensive and suffers from significant disabilities in terms of protecting the professional office from credit card problems.

The number one financial obstacle faced by healthcare providers is that often they do not get paid for services rendered because of the traditional paper billing system employed. Statistically, 30% of revenue comes directly from patients and not from other payers like insurance companies or a patient's employer. Patient balances sit on the healthcare provider's account for an average of 4 months. Traditional paper billing and collection methods result in a recovery rate of only 50%. The cost of billing a patient is between $7.00 and $9.00 per bill in administrative time, postage and supplies. Generally, a doctor's office must send out an average of three statements to get one bill paid. The number one way a doctor loses a patient to another doctor is to allow that patient to owe money because the patient then becomes embarrassed or angry and leaves the practice. It is important to note that studies show the average patient will refer as many as eight other patients to a practice. However, this can only happen if a patient is on good terms with the practice. Generally, consumer surveys show that vacations and charitable contributions take precedence over payments owed to doctors and dentists.

While there are other companies which offer payment services using credit cards to healthcare professional, these other services utilize a one payment processor, which is hard coded into the practice management software. This single payment processor normally has a set price and a "kickback" to the software distributor for any software sign-ups. These other technologies do not integrate with the practitioner's choice of practice software, forcing them to open a separate program to process payment from another, preferred credit card payment processor.

The healthcare industry is not differentiated from other industries in the eyes of payment processors. All processes have the same cost, but they don't have the same overhead. Processors who service many different industries may have fraud losses associated with the different industry, but charge the healthcare providers the same rates as the other businesses, which have substantial charge-backs and other fraudulent activities. Generally, retail businesses have much higher fraud and return/cancellation issues than do healthcare providers. This becomes a significant problem to healthcare providers as they are forced to pay increased rates to the credit card processors due to the retail market's failure to differentiate between industries.

Accordingly, there is a need for an improved payment processing bridge which can be joined to and integrated with a wide variety of practice management systems and to allow payment processing at a reduced cost associated with the specific risks inherent to the healthcare industry, without the need for a user to exit the practice management software, perform additional steps or enter the payment information into multiple systems. Also, there is a desire to be able to optimize a healthcare provider's selection of a payment processor independently of the forced deal imposed by their practice management software vendor. And there is a need for a payment bridge which seamlessly bridges the healthcare professional's practice software and their patients use of credit cards in a way which minimizes the costs, enhances the convenience and provides a robust safe environment for the healthcare professional and their patients.

SUMMARY OF THE INVENTION

The invention is directed to a Payment Bridge allowing for a payment processing system which can be selected and integrated with a wide variety of practice management software systems, including those which impose a required payment processing option, without the need for multiple or duplicative entries of payment information. The Payment Bridge includes software for enabling payment processing on an automated and highly reliable level which integrates with the payment parameters of practice management software such that payments made through the Payment Bridge automatically populate the relevant bookkeeping fields of the practice management software.

Another object of the invention is to assist in preserving and enhancing the doctor/patient relationship by teaching discrete, comprehensive methods of getting paid at the time of treatment using an exclusive and specialized credit card processing program.

A further object of the invention is to provide improved integrated processing of credit card transactions for healthcare providers incorporating specialized processes tailored to healthcare providers.

Still another object of the invention is to provide improved integrated payment processing of credit card transactions without treating healthcare providers as high risk retailers.

Yet a further object of the invention is to provide an improved Payment Bridge which is middleware that is fully compatible to be integrated with a wide variety of medical or dental practice management software selected by the practitioner and a low cost credit card processor.

Yet another object of the invention is to provide a practitioner having proprietary practice management software with an integrated Payment Bridge which can be configured to be compatible with the proprietary practice management software and allow the practitioners to centralize all methods of patient payment for all delivery sources within a secure environment.

Still a further object of the invention is to allow a payment to include those initiated in a kiosk, mobile and IVR phone, tablet, API and billing companies or back office operations, all integrated with the practice management software.

Yet still a further object of the invention is to provide a Payment Bridge which acts as a plug-in providing a simple user interface that accepts payments while simultaneously updating client ledgers and bookkeeping ledgers in the practice management software being utilized by the healthcare professional.

Yet another object of the invention is to provide enhanced features vital to medical and dental payment processing software such as card-on-file, recurring payments and transactional reporting, all via the patient portal of the Payment Bridge.

Still another object of the invention is to provide a Payment Bridge with a vault feature which employs front and back end encryption technology that removes liability from the provider's office or the card holder, rendering it impossible for any third parties or even practitioner office employees accessing a patient's credit card information through the Payment Bridge.

Yet still a further object of the invention is to utilize a vault system wherein all saved information is stored on secure offsite servicers, which makes the information stored safely and securely, while providing convenience for both the patient and the practitioner, whereby the access to the vault can be limited to system administrators.

Still other objects and advantages of the invention will, in part, be obvious and will, in part, be apparent from the specification.

The invention accordingly comprises the features of construction, combinations of elements and arrangements of part and processes which will be exemplified in the constructions and processes as hereinafter set forth, and the scope of the invention will be indicated in the claims.

BRIEF DESCRIPTION OF THE DRAWINGS

The present invention will now be described in more complete detail with frequent reference being made to the figures identified below.

DETAILED DESCRIPTION OF THE PREFERRED EMBODIMENTS

Figure 1:
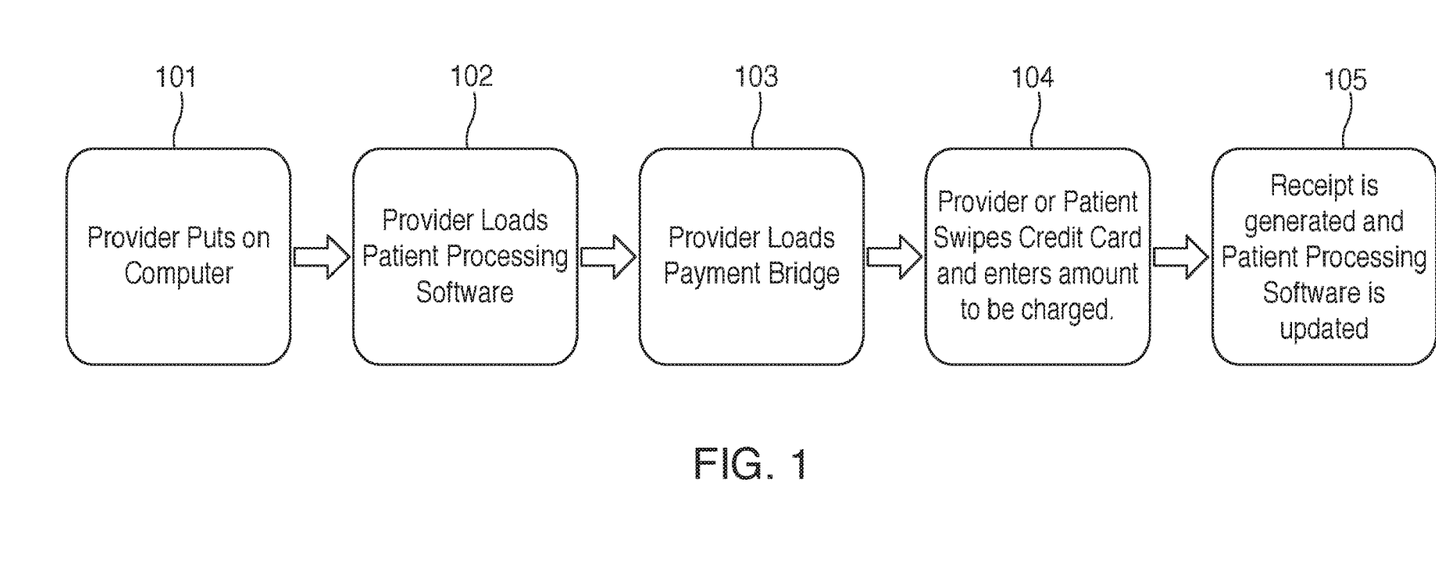
FIG. 1 is a functional flow diagram of the summary fashion by which the Payment Bridge

Reference is first made to FIG. 1, where a general flowchart diagram describing the manner in which the Payment Bridge is utilized is depicted. Starting at block 101 in FIG. 1, the provider puts a computer onto his or her network and in block 102 loads their patient processing software. The patient processing software, also known as practice management software is loaded so that it is functional on the provider's computer. Next, in block 103 the provider loads the Payment Bridge middleware onto the computer. The Payment Bridge middleware can be loaded on any computer being utilized, including the traditional Windows, Mac and Unix and other operating system computers. The Payment Bridge, when it is loaded, can be integrated with any practice management software that the provider chooses. The Payment Bridge is open and running the background of the computer and does not disrupt any of the software processes of the practice management software. The Payment Bridge is compatible with both the various credit card scanners available on the market and any gateway provider of credit card processing.

In block 104 of FIG. 1, the provider or patient swipes the credit card and enters the amount to be charged and, finally, in block 105, a receipt is generated and the patient processing software is updated to reflect that payment has been received. The Payment Bridge is compatible with any credit card scanner available and any gateway provider. Generally, the Payment Bridge only takes about 7 seconds from the time payment is submitted to process the payment, generate a receipt and update the system. No special activities are required and no multiple entries are necessary as the Payment Bridge handles the interface with the practice management software to update the appropriate ledgers for the patient and for accounts receivable and for collections.

Generally, prior payment solutions often timeout or require separate authorizations before processing a transaction. Once the Payment Bridge is loaded it runs in an awake state in the background, only appearing when a credit card is swiped and does not shut down until manually shut down. All transactions are done at the local level via the provider's computer, while all the configurations are done at the server level. Transactions include the physical swiping or entering of credit card information into the card reading device. On the local level, the amount to be charged is entered, and the signature is accepted. The transaction occurs on the computer but the processing happens at the gateway. All transaction information is input and updated on the client's practice management system via the Payment Bridge. Once a credit card is swiped, the Payment Bridge encrypts that information and sends only the encrypted information to the card processor, so that unencrypted credit card information is never saved or transmitted.

Figure 2:
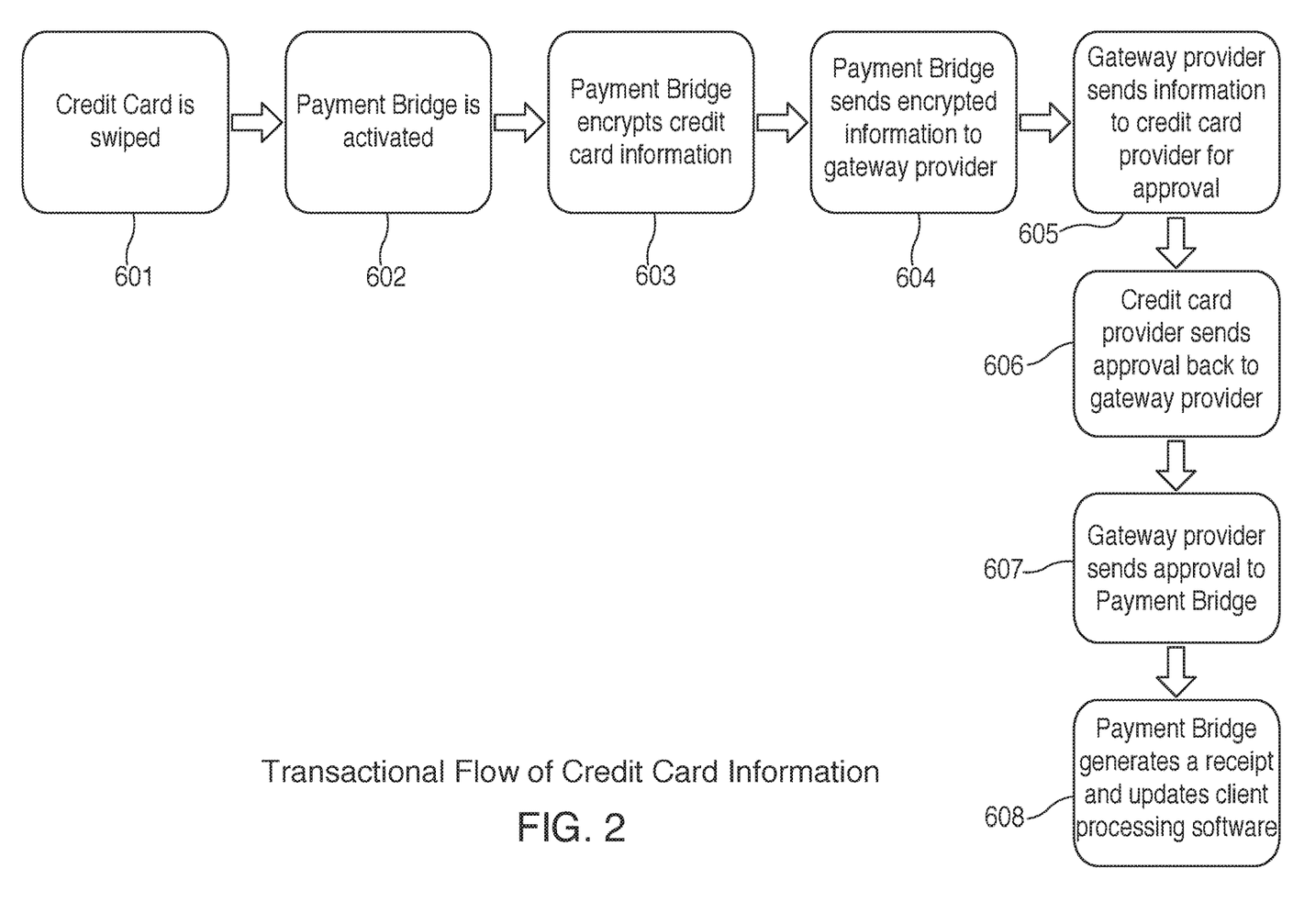
FIG. 2 is a transactional flow diagram of credit card information in functional block diagram form, in accordance with the invention.

Reference is next made to FIG. 2 wherein a more detailed flow chart diagram showing the transactional flow of credit card information in accordance with a preferred embodiment of the invention is depicted. Starting with the upper left, an employee or the patient swipes the credit card through a credit card scanner in block 601. This then activates the Payment Bridge middleware which comes to the fore at the user's computer screen in block 602. Next, the Payment Bridge encrypts the credit card information in block 603 and then the Payment Bridge sends the encrypted credit card information to the gateway provider in block 604. The gateway provider sends the information to the credit card provider for approval in block 605. When the credit card provider sends the approval back to the gateway provider in block 606, the gateway provider, in turn, sends an approval to the Payment Bridge and the Payment Bridge in block 607 finally generates a receipt for the patient and updates the client processing software as noted above in block 608.

When the Payment Bridge is initially set up and configured, three levels of authentication are required to operate the Payment Bridge software.

First, the provider's computer must be installed by the Payment Bridge technical staff, which configures the provider's computer with a specific name, mac address, and hardware configuration data which will be used to validate processing with the Payment Bridge application server. A computer that is not configured by the Payment Bridge staff and not added to the "allowed" list, cannot launch the Payment Bridge software. This prevents third parties or hackers from accessing the system or attempting to process credit card transactions that are not authorized.

Second the Payment Bridge application users are provided credentials for the application that relate to server based data storage. No items are stored locally. The practice name, address, settings and other configurations are maintained in the Payment Bridge Application Server, remotely from the provider's computer. This assures that if a hacker gains access to the provider's computer, he is unable to modify or corrupt the data or obtain access to any credit card information.

Third, there are PCI Level One Gateway credentials issued by the Payment Bridge staff. The Payment Card Industry Data Security Standard (PCI DSS) is a set of requirements designed to ensure that all companies that process, store or transmit credit card information maintain a secure environment. Essentially any merchant that has a Merchant ID (MID). PCI Level One means any merchant—regardless of acceptance channel—processing over 6M Visa transactions per year.

The user based security allows for various system functions, as well as secured transmission with the PCI Level One Gateway.

The Payment Bridge application server stores a unique integration key for a variety of different practice management software systems. Every practice management software configuration key is stored and updated based on the version releases of the practice management software offered in the market place. Each configuration key is replicated and customized for each merchant so that the Payment Bridge software works with the version and configured practice management software actually running on the provider's offices. Information found on the configuration key is the necessary information to post a transaction. This includes, but is not limited to, a payment amount, the card type that is being used, and a transaction ID. This information can be customized and configured for any practice management system to input any information that the provider would like. Also, the configuration can be replicated and used on other practice management systems. The Payment Bridge application server contains no credit card transaction data. The integration keys and configuration data are downloaded upon every successful log-in to the Payment Bridge, not separately for each transaction. This way, whenever an update has to be made, it is done at the application server level, so that when the user logs onto the system, the Payment Bridge will be updated to the appropriate version of the practice management software being utilized. So, while the Payment Bridge is running locally in the healthcare professional's office, the "guts" of the system are being run on the Payment Bridge application server, which is remote from the healthcare professional's office, to protect against intrusions and problems which might occur at the healthcare professional's office.

The Payment Bridge application server uses the multi-site Payment Bridge controlled Amazon Web Services instance that uses Advanced Encryption Standard (AES) 256, a secure symmetric-key encryption standard using 256-bit encryption keys for storage. All Amazon Web Services hosting facilities are compliant with SOC 1/SSAE 16/ISAE 3402 (formerly SAS 70 Type II); PCI DSS Level 1 and HIPAA. The HIPAA standards are well known related to the portability of client data and the confidential and secure treatment of client data in the health care fields. HIPAA stands for the Health Insurance Portability and Accountability Act. The Payment Bridge has been configured to operate on 3 distinct US Amazon Web Services instances such as the US East (Northern Virginia), US West (Oregon) and US West (Northern California). Other cloud services providers could be used as well.

In relation to the use of the system, there is a further description of the outflow transaction and the inflow transaction. We start with the outflow transaction. First, is the card acceptance at the provider point of care. There are generally two preferred methods of inputting data in accordance with the invention. In the first, there is use of a VeriFone Mx-915 scanner, where the credit card never leaves the patient's possession. The swipe data is securely obtained from the credit card. The device is programmed to only accept Payment Bridge programming and to support end-to-end security with VeriShield Total Protect, secured by RSA, which eliminates sensitive cardholder data from the payment device and merchant infrastructure through Tokenization. The second method is to use a MagTek.scanner. RSA is a two-factor authentication technology that is used to protect network resources. The authentication is based on two factors—something you know (a password or PIN) and something you have (an authenticator). The authenticator is typically a hardware token (such as a USB token, smart card or key fob) and the software token is the RSA Authentication Manager Software that provides the security engine used to verify authentication requests. When a user attempts to access a protected resource, he is prompted for a unique passcode. The passcode is a combination of their user's PIN and the code that is displayed on the authenticator token at the time of log in. The user ID and pass code are intercepted by the RSA Authentication Agent and presented to the RSA Authentication Manager software which validates the pass code. The RSA SecurID system computes what number the token is supposed to be showing at that moment in time, checks it against what the user entered, and makes the decision to allow or deny access.

In this approach, the credit card is quickly handled by the Payment Bridge trained provider's office staff. Swipe data is, again, securely obtained from the credit card. This system is specifically designed to meet PCI DSS requirements to secure cardholder data, the Dynamag employs the industry standard, Triple DES encryption. Second, the device submits encrypted data to the Payment Bridge application installed on the provider's computer. The encrypted data, along with user entered data, is never stored in the Payment Bridge on the user's computer system. The encryption is done via MD5. MD5 is an algorithm that is used to verify data integrity through the creation of a 128-bit message digest from data input (which may be a message of any length) that is claimed to be as unique to that specific data as a fingerprint is to the specific individual. MD5 is intended for use with digital signature applications, which require that large files must be compressed by a secure method before being encrypted with a secret key. It is relayed via standard HTTP protocol over an SSL connection to the PCI level one data center/gateway provider.

Third, the PCI Level One Gateway provider is certified to submit, store, and tokenize data. The gateway service providers that store, process or transmit encrypted cardholder data must demonstrate PCI DSS compliance and provide the compliance validation to all card brands annually. In addition, the gateway service providers must annually certify to processor security standards. Finally, the gateway provider maintains multiple redundancies in connectivity, carriers and telecommunication companies, and a network of SAS-70 (a widely recognized auditing standard) for datacenter facilities.

Fourth, the processing entity receives and decrypts data. Once received by the payment processor, the card data is decrypted and sent to the card networks for processing. No decryption/re-encryption is necessary until Vantiv (or another payment processor) receives the transactions, providing enhanced security for the entire process. Vantiv, Inc. is a U.S.-based payment processing and technology solutions provider headquartered in the greater Cincinnati, Ohio area. Vantiv is the largest PIN Debit U.S. acquirer and third largest U.S. merchant transaction acquirer ranked by general purpose transaction volume. The Company provides payment and technology services to merchants and financial institutions of all sizes in the U.S. and processes more than 16.9 billion payment transactions and approximately $611 billion in volume annually. As of 2014, Vantiv supports approximately 400,000 merchant locations and more than 12,000 automated teller machines (ATMs) in 46 states and eight countries.

Next, we focus on the inflow transaction where, the first step is the processing entity response data. The response data contains no secure cardholder information. Next, the PCI Level One Gateway receives response data and tokenized card information from the processor. The tokenized data and card information is stored in adherence with PCI security standards.

Next, the Payment Bridge application receives response data from the PCI Level One Gateway. The response data is utilized to generate a PCI compliant receipt and then the compliant receipt is stored on the Payment Bridge application server for retrieval and backup.

Finally, the response data is utilized to enable practice management key configuration for posting back to the practice management system. No card data is available or available for request posting back to the practice management system. In other words, the card data is not stored in any fashion on the application server or the provider's computer.

Additional functionality can be utilized since it is possible for the credit card data, which has been encrypted, to be retained for use in the future if authorized the patient. This allows the provider to charge the patient's credit card without the need to separately swipe the credit card if authorized by the patient. Similarly, where a provider and patient agree to a recurring payment to pay for services, the patient can, by a separate agreement with the provider, authorize a series of payments utilizing the credit card at specified intervals of time. Thus, a patient might agree to pay a $500 bill at $100 per month, payable on a particular day of each month. The system can be set up to enable this system by retaining the access to the scanned credit card information which is stored in encrypted form at the PCI Gateway vault in a securely encrypted form.

Among the additional features which are available through the Payment Bridge are the ability to use manual checks, enhanced transaction searching, EMV/Chip Card processing, a digital pre-authorized health care form, custom receipts, a patient vault and support ticket submission.

Manual check processing to the payment bridge to help offices take checks without the use of a check reader is an important feature. Check readers are often clunky, and are not well-received in the industry. We added a streamlined window into Payment Bridge so that you can enter in checks manually with the check's credentials. Entering in the checks routing number, account number, name on account, and payment amount allows you to process the check electronically without the need for a check reader.

There have been enhancements to the Transaction Search window which has improved functionality substantially. There are more search fields/parameters and ways to customize the search. The functionality to search by a specific processor is a big step into giving the end-users more control over their reporting. The ability to customize the orientation of the results and in what order they display on your screen has been added. Furthermore we have improved the export function so that it generates printable reports more efficiently. We have reformatted the printable report to include a break down with totals while still including the full transaction detail. We have also added the ability to include or exclude certain fields when you choose to export a printable report rather than being forced to export every known value of the transactions. This allows for more control over the reports from the end-user.

EMV or Chip Card functionality has been added to Payment Bridge. This is the new standard mandated by the banks and the Payment Bridge is the first product to have EMV transactions successfully running through a software and processing through a gateway. The newest model of terminal we are rolling out—the VeriFone MX915—comes ready with a Chip Card slot that we utilize and sync with our normal Payment Bridge check-out process. We are the first company in the nation to have EMV/Chip Card transactions functioning through a software processing on a gateway and automatically posting to a merchants practice management software on their office workstation.

In the past we have always provided our merchants with a "Pre Authorized Health Care Form". This form is used to create a contract with a patient to leave their card on file for a payment plan or a charge later down the road. We have now integrated this form electronically into the Payment Bridge. A patient can pull up a sample form and fill out all the relevant information including: Practice Name, Patient Name, Card holder name, Billing Address, Card number/expiration, and Payment plan details. Once submitted Payment Bridge will create the form with all the entered information and then allow the patient to electronically sign it via a VeriFone MX915 Card processing unit. Once signed the system stores the form—including the TRUNCATED card number—and puts in on a secure server. Nothing is saved locally on the merchant's workstation. This allows them to use our search form function to pull the form they want to review from the server from any computer Payment Bridge is installed on without the risk of having a patient's confidential information, including the credit card number and expiration date, stored locally or accessible locally.

Our Receipts are customized per merchant through our Gateway Configuration Manager. Receipts are localized to a specific workstation's configuration. This allows us to change receipt settings on a case-by-case basis within workstations of the same business. If we have a business with two different check-out stations we can have one computer display different receipt settings than another based on merchant request. The receipts are fully customizable with company Logo and information able to be added. They are stored on a remote server and able to be searched in the system from any computer with Payment Bridge on it. A merchant can pull any old receipt they have ever generated. The system also allows for emailing the receipt directly from Payment Bridge's interface as well as printing it. We can further customize the printed receipts by providing a thermal receipt printer and formatting them to print as a standard sized receipt, or increase the size for the receipt to properly print out of the merchants personal printer with 8.5"×11" paper.

The gateway provider we utilize has an option for storing patients' credit cards and assigning a unique ID to them called the "Patient Vault". We have now integrated with this feature by allowing our merchants to utilize our Payment Bridge to both create and easily charge a stored card and vault ID via an API to the gateway. During any live transaction a merchant has the option to select "Add to vault" and store the card. Upon doing so they will also choose a "Vault ID" which will allow them to select a customized way to identify the stored card without the need to use the patient's actual card numbers. The card will be securely stored in the gateway, and neither the merchant nor our own staff have access to the full card number. If the merchant wants to charge the stored card they can utilize the "Vault Transaction" feature to pull up a simple window that will allow them to search for a stored Vault ID, select an amount, and charge the stored card very quickly.

A support option has been added to Payment Bridge's main menu to allow merchants to submit an emailed support ticket directly to our technical support team if they have an issue. This feature was added in order to streamline the ability for the merchant to get help when they need it. The window lists the normal support number so it is always readily available for the merchant to call. If for some reason the merchant cannot make a phone call directly to the tech team, they can utilize the support ticket window to describe their issue, put down which office they are from and a call back number and send it off to our team. Once submitted there is an average 30 minute wait time for a technician to receive the request and call back the office ready to help them solve the issue.

Figure 3:
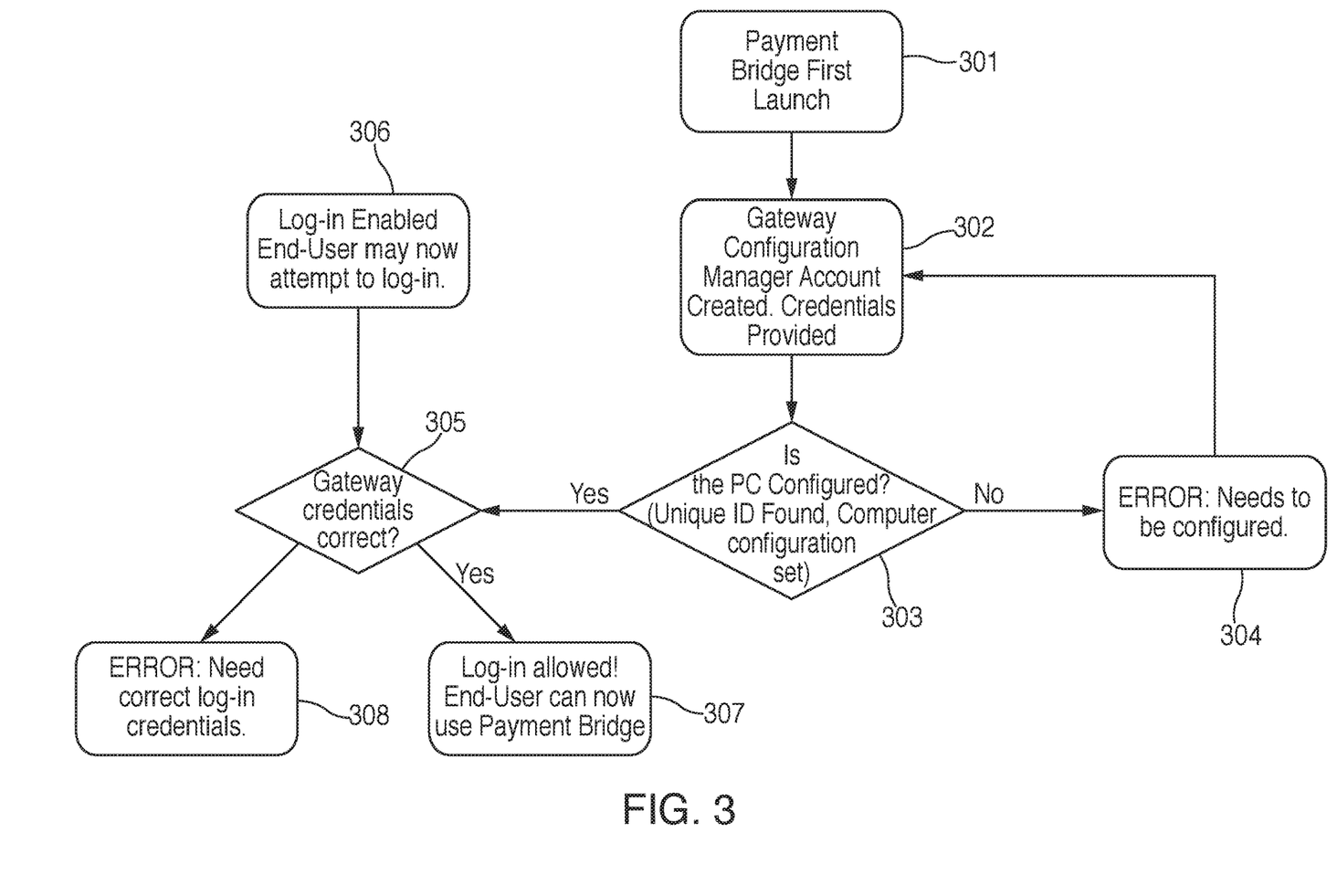
FIG. 3 is a functional flow diagram of the way that the Payment Bridge is loaded and used by the user.

The Payment Bridge authenticates on several different levels. FIG. 3 shows the Payment Bridge's process in allowing an end-user to access the system and what needs to happen in order for access to be granted. The process starts with the first launch 301 with an authorized IT technician installing the software on the client's computer 302. Once installed the Payment Bridge isn't immediately useable—it needs to be set up and configured within several different systems.

First, if not already configured, it needs to be initially launched (301)—this pings the Payment Bridge's server and lets us know a new device is attempting to connect through Payment Bridge. Upon launching the first time an error message stating that the computer "needs to be configured" will show. This needs to be seen at least once in order to ensure the Gateway Configuration Manager has picked up the computer. Once the computer has been found in the system, the system will automatically assign a Unique Identification to the computer in block 303. This identification is taken from the computers various pieces of hardware and is a combination of their MAC Addresses, serial numbers and other values. It is intended to be unique at all costs. This is to ensure every computer in the system is completely unique and access to the system is only given on a case-by-case basis. If by some chance two similar systems generate the same name, we can implement a customized string onto the Unique Identification to ensure it is not duplicated. At this point we need to now give the computer permission to access the system.

First a Gateway Configuration Manager account needs to be created— this consists of creating an internal username/password used to tell the system what account the computer belongs to. Once this is done the actual configuration of the computer needs to be accessed. Once accessed the internal username/password created is entered in here. Additionally, we will customize the computer's settings at this point. These settings consist of Receipt configuration and mock-up, selecting the proper Credit Card Hardware attached, printer settings and advanced features for the linked credit card terminal. If it is determined that the PC is not properly configured the flow goes to Block 304 and back to Block 302.

Once the computer is all configured, Payment Bridge can be relaunched. Now it will bring the end-user to a log-in window 305, rather than throwing an error message. At this point the user required log-in credentials from the gate-way provider in order to access the software. This is normally set up before hand, an account needs to be created in the gateway linking their bank account, practice information, and a username/password. If this is not done the user will be unable to log in and will be given an error message "Login Failed! Please Try Again." Once this is provided, and the above steps have been completed, the end-user can use the credentials to access the system. If the correct credentials are supplied the flow shifts to Block 307 and the user can use the Payment Bridge. If not, it goes to Block 308 and new credentials need to be used.

After the first setup and login the user would enter the login process at Block 306, avoiding the setup sequence. From there they enter the Gateway credentials and if appropriate can start using the Payment Bridge.

The Payment Bridge and our Gateway Configuration Manager combine with a Gateway Provider to give us supreme flexibility and customization of the accounts we create. The Secure Gateway Service we use allows for accounts with multiple Merchant Identification Numbers attached, to create an account for multiple businesses. We can utilize a combination of the tools within the Gateway, our Payment Bridge Software and our Gateway Configuration Manager to customize these accounts in many ways. The "Multi-Merchant" screen within the Gateway Configuration Manager gives us the ability to customize the business that is selected by the end-user upon making a payment in Payment Bridge. This gives us full control on Multi-Merchant accounts to customize which businesses the end-user can access.

The end-user can be given a drop-down menu during the transaction that lets them choose where the payment they are making is associated. For example, a business may have three entities: A, B and C. In this drop down we can allow the end-user to choose if the payment should be associated with entity A, B or C. Further we can create extra options that, on the back end, route to the same MID and bank account but will display differently in the window. This allows us to have, for example, Entity A, B, C and D. Choosing A and D for example may route to the same bank account, but will display a different name on the transaction and receipt for reporting and book keeping reasons. We can further customize this with Merchant Defined Fields. We can create any extra fields the merchant would desire during a transaction for extra information. For example a field of "Patient Name" is a common request so that the end-user can type in the Patients Name separate from the card holder's name. This may be used to separate a child who is the patient from the mother who is the card holder when looking at the receipt later. The custom Merchant Defined Fields can be free text boxes (as the previous example was), Radio Dials or a drop-down selection. The power of our system even lets us take this a step further and attach merchant defined fields to the transaction itself. Meaning when choosing a certain merchant defined field, it may effect where the transaction routes to. This can be used as an alternative to our normal Multi-Mid drop-down to give large organizations with lots of entities more flexibility in how their end-users make a payment.

We use keyboard emulation scripting to integrate and post to other software. Our tech team is trained in the Payment Bridge's own scripting language to be able to customize and create any string of commands necessary to post to another software. This feature is directly tied in with our Gateway Configuration Manager and we utilize the "Application" section of the GUI to write the script. Our scripts are simple in nature, but can become complicated during design. We can customize the script to allow the keyboard emulation to post to virtually any software there is. Our tech team can run through the posting manually and figure out what keystrokes are needed to post—and then replicate those keystrokes within the Configuration Manager's GUI. A basic script, for example, may require multiple steps to post an Amount, Card type, and Transaction ID. For example—the technician may have the script start in the amount field. Payment Bridge will then enter the amount→tab 3×→enter card type→tab 1×→enter Transaction ID. This is the most basic of integrations. We can have it enter more fields, enter in the same value in multiple fields and even customize and stack more than one script so that posting can be done in more than one window. Our posting is secure in that it will not post if the correct window isn't located. Authenticating the actual window we are interacting with allows us to ensure that mistakes in the system don't happen.

For example, a script may be written to recognize a window called "Add a Payment" in a practice management software. If a merchant did not open the correct "Add a Payment" window before processing the transaction, when it comes time for the system to auto-post it will sense the desired window is not available. When this happens, the system will still correctly process the transaction and generate a receipt, but it will not post the information. The information can always be manually posted, or auto posted at a later time, so nothing is lost on the merchant's end. This means that accidental key-presses and typing don't happen in an unintended environment. The ability to authenticate with the actual window also allows us to create multiple integration set-ups. If a software has more than one screen that an end-user can post a payment to, we can set up multiple integrations to account for this. If there is payment screen A and B in a software, we will build integration A and B respectively. If they are attempting to post to payment screen B, the Payment Bridge will begin to check if the requirements are met to begin running Script A. It will then find that the window needed for Script A is not available, it will then switch over to Script B and check if posting can be done. Once it finds and authenticates that payment screen B is available, it will proceed to run Script B. We can extend this to any number of scripts we want.

Since the development of the Payment Bridge one of our focuses was automatic posting of transactions to the merchant's practice management software. This was always done in a single direction, however we have now launched bi-directional integration. What this means is that we are no longer restricted to simply posting our information to a practice management software. We can now also pull information from the software before the transaction is even made. For example, if a patient has an outstanding balance of $30 for a co-pay in the merchants Practice Management Software, before bi-directional integration the merchant would have had to manually enter the $30 and relevant patient information into our system. With bi-directional integration we can have the system pull information such as outstanding balance, patient name, patient account number and more into our system upon generating a payment. This means all the merchant has to do is begin the process of starting a payment, quickly review the information and amount automatically pulled from their practice management software, process the payment and then allow our system to automatically post the payment back into their software. This feature gives flexibility to work and integrate with systems no other processor can integrate with. It opens the door for extreme customization in the way a merchant takes and processes payments, and drastically cuts down on the human-input needed during a transaction.

We have recently had an advancement in our integration technology to seamlessly be able to post to web-based software. We have always been able to post one way to certain web-based applications, but our new Google Chrome Extension allows us to not only seamlessly post to most web-based applications, but allows us to do bi-directional integration on them as well. Our Google Chrome extension is easy to install via a direct link we provide to the Chrome Web Store. Once installed it runs in the background and allows the Payment Bridge to communicate with the web browser. When a card is swiped Payment Bridge is able to recognize that the extension is installed by putting focus on the title of the current active browser tab. This tab is updated with relevant information related to the transaction, which the Payment Bridge is then able to pull into its payment screen. For example, the most common parameter to use for bi-directional integration is the payment amount due. The merchant's practice management software will have a recorded balance for the patient of how much they owe, this will be updated into the browser tab and allow Payment Bridge to automatically fill in the payment amount upon the start of the transaction, saving the end-user the time to enter it in themselves.

Figure 4:
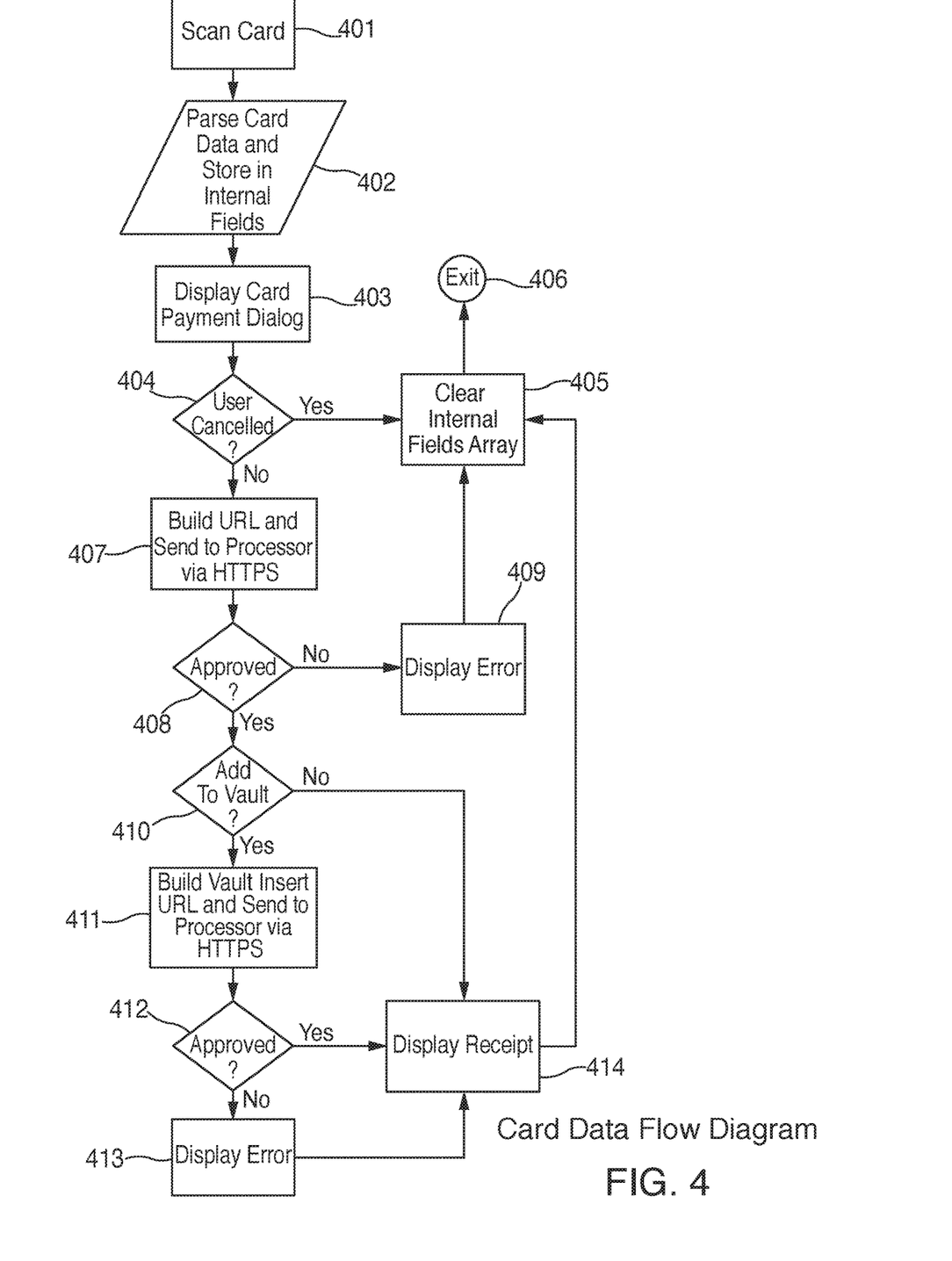
FIG. 4 is a functional flow diagram of the card data flow in the Payment Bridge in accordance with a preferred embodiment of the invention.
Figure 5:
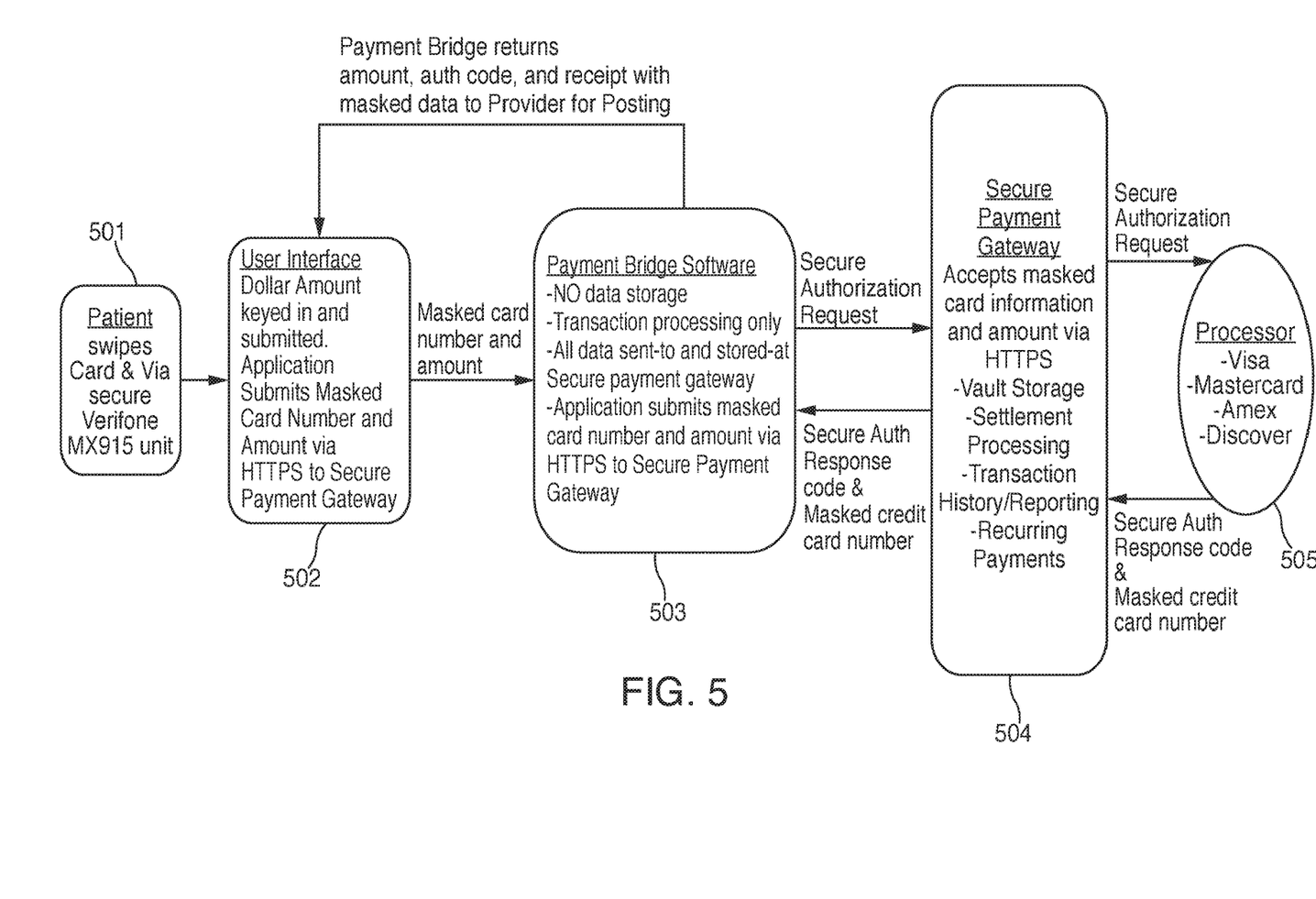
FIG. 5 is a transactional flow diagram of the flow of credit card information from the Payment Bridge to the credit card processor seeking approval and receiving that approval back from the credit card processor in accordance with a preferred embodiment of the invention.

We now focus on the Card Handling features of the Payment Bridge which are critical to its ability to function in the processing of credit card payments in the system. The handling of sensitive credit card data needs to be done securely and quickly. The Payment Bridge only holds this information in its temporary memory as long as required to send the transaction directly to the processor. It is never stored in an unencrypted form in any permanent memory within the Payment Bridge at either the user's or our computers, only at the actual payment processor. Reference is made to FIGS. 4, 5 and 6 which show the Card Data flow diagram, the way in which the card swipe is processed, and the transactional flow of credit card information.

The flow charts of FIGS. 4, 5 and 6 will describe the process of transmitting credit card data and retaining a response from the merchant processor. Only credit card transactions will be discussed with reference to these Figures, although ACH transactions are handled in a very similar fashion.

With reference to FIGS. 4, 5 and 6 these figures show how data flows from the Payment Bridge to the merchant account processor. Although the processor may be different the flow is exactly the same for all of them. At no point in the process is card data stored or displayed in full. Account number or PAN is displayed with only the card's final 4 digits. None of this information is stored in any log file or debug output. Essentially the key is that the full account number is encrypted and only that encrypted account number is actually transmitted. Nowhere on the Payment Bridge or Gateway server are the unencrypted account number maintained.

With reference to FIG. 4, the card data flow is described from start to finish, generally ignoring any path that results in a cancelled transaction. The flow starts with a scanning of the credit card in block 401, the parsing of the card data and storing temporarily in internal fields in block 402, and display of the card payment dialog by the Payment Bridge in block 403. If it is determined in block 404 that the User has been cancelled, the flow directs to block 405 where the internal fields containing the credit card data are cleared and the transaction is exited in block 406.

Assuming the User has not been cancelled, the flow proceeds to block 407 where the Payment Bridge builds a URL and sends the card data (in encrypted form) to the Processor via HTTPS. In block 408 the system waits to see if the processor approves the transaction. If not, in block 409 an error is displayed and the flow reverts to blocks 405 and 406 where data is cleared and the system exited.

On the other hand, if the transaction is approved, the flow continues to block 410 where it is determined if the card data should be added to the card data vault. If not, the flow proceeds directly to the block 414 where a receipt of the transaction is displayed and then printed. If the card data is desired to be added to the card data vault, in block 411 the system builds a vault insert URL and sends it to the Processor by HTTPS. If this is approved then the system proceeds to display and print a receipt of the transaction in block 414 and finally clear the internal fields away in block 405 and exit the system in 406. If the vault insert is not approved an error is displayed in block 413 and the receipt is displayed in printed in block 414 followed by the clearing of the internal fields and exit in blocks 405 and 406.

A card swipe initiates the credit card transaction. When a card is swiped the track data is parsed and a window is displayed containing First Name, Last Name, Obfuscated PAN (Last four digits) and Expiration Date. It is here the user enters the transaction amount, merchant defined fields and other data required to complete the transaction.

When the user presses the Send button the transaction is built in memory. This is done by either creating a URL containing the request data or a web service object and setting its member data. Either way this is accomplished the request is sent to the processor via a 128 bit SSL connection. We then wait on the same connection for a response from the processor. This response contains only a result code, transaction ID and a few other status fields. The processor never returns credit card data in its response.

The storage of the data in the credit card vault is a user selectable option that will add the payment method to the client/customer vault on the payment processor's system. If this option is selected and the transaction is successful a second request is built and transmitted in the same manner as the initial transaction request. This request is sent directly to the processor using 128 bit SSL encryption.

A printable receipt with signature line is displayed to the user if the transaction is approved. If the transaction is declined the receipt contains the reason for decline as reported by the processor. This receipt only displays the final four digits of the PAN.

No matter how the transaction exits the approval process the memory is cleared of any card holder data immediately. This process involves not only releasing the memory being used, but first over-writing the data with random characters prior to release. This gives the added protection of having random data in the memory blocks used prior to freeing it back to the system for re-use.

Reference is next made to FIG. 5 wherein the flow between the card swipe and the Processor is shown in flow chart form. In block 501 the patient swipes the credit card via a secure credit card machine which can handle either a swipe or by insertion in the case of a chip enabled credit card. Next in block 502 the user keys in the dollar amount to be charged in the transaction. The application submits the masked card number and amount via HTTPS to the Scure Payment Gateway. This is submitted to the Payment Bridge in block 503 which has no data storage, but only transaction processing. All data sent to and stored at the Secure Payment Gateway arrives as masked card number and amount. This is forwarded to the Secure Payment Gateway which accepts the masked card information and amount via HTTPS and performs the vault storage, settlement processing, transaction history and reporting, and recurring payments. Finally, this information is passed to the processor in block 505 to secure an Authorization Request. The processor replies with a Secure Authorization response and the masked credit card number, which is passed back to the Payment Bridge software in block 503 which in turn passes the amount, authorization code and receipt with masked data to the Provider for posting.

Finally, with reference to FIG. 6 we show the transactional flow of Credit Card information. Starting in block 601 the Credit Card is swiped. This leads to block 602 where the Payment Bridge is activated and block 603 where the Payment Bridge encrypts the credit card information. In block 604 the Payment Bridge sends the encrypted information to the gateway provider. In block 605 the Gateway Provider sends information to the credit cared provider for approval. In block 606 the credit card provider sends approval back to the Gateway Provider. And, in block 607 the Gateway Provider sends the approval back to the Payment Bridge. Finally in block 608 the Payment Bridge generates a receipt and updates the client processing software.

Accordingly, an improved Payment Bridge which provides for enhanced security, improved performance in compliance with the highest levels of security and HIPAA requirements is provided. The system is designed to integrate with whichever practice management software the provider utilizes in a fashion which makes the use of the Payment Bridge system and the ability to select different credit card payment processors from those required by the practice management software without loss of functionality.

It will thus be seen that the objects set forth above, among those made apparent in the preceding description, are efficiently obtained, and, since certain changes may be made in the above construction without departing from the spirit and scope of the invention, it is intended that all matter contained in the above description or shown in the accompanying drawings shall be interpreted as illustrative, and not in a limiting sense.

It is also understood that the following claims are intended to cover all of the generic and specific features of the invention herein described and all statements of the scope of the invention, which, as a matter of language, might be said to fall therebetween.

What is claimed is:

1. A payment bridge system for a service provider, comprising:
   an application server that stores a plurality of unique configuration keys, wherein each unique configuration key comprises a set of computer readable instructions executable by a computer to emulate the commands required to communicate with a respective type of practice management software, wherein each respective type of practice management software comprises a respective set of computer readable instructions that are executable by a computer to provide business management functionality, including generating invoices and bookkeeping functionality;
   a service provider computer system located remote from the application server and in communication with the application server for receiving one or more unique configuration keys;
   a first type of practice management software installed on the service provider computer system, wherein the first type of practice management software comprises a set of computer readable instructions that are executable by the service provider computer system to provide business management functionality, including generating invoices and bookkeeping functionality; and
   a payment bridge installed on the service provider computer system, wherein the payment bridge comprises a set of computer readable instructions executable by the service provider computer system to:
      receive credit card transaction information for a requested credit card transaction involving payment of an invoice generated by the first type of practice management software, wherein the credit card transaction information comprises credit card information and payment amount,
      transmit the credit card transaction information to a gateway provider of a credit card payment processor,
      receive a response from the gateway provider, and
      communicate with the first type of practice management software to update the first type of practice management software with information associated with the requested credit card transaction if the requested credit card transaction is approved, wherein the payment bridge communicates with the first type of practice management software using a unique configuration key for the first type of practice management software received from the application server.

2. The payment bridge system of claim 1, further comprising a credit card scanner in communication with the payment bridge for receiving credit card information from a credit card that is scanned by or inserted into the credit card scanner.

3. The payment bridge system of claim 2, wherein the payment bridge encrypts the credit card information received from the credit card scanner before transmitting the credit card information to the gateway provider.

4. The payment bridge system of claim 3, wherein neither the payment bridge and nor the service providers computer system store unencrypted or encrypted credit card information after it has been transmitted.

5. The payment bridge system of claim 1, wherein the payment bridge updates the first type of practice management software after the requested credit card transaction is approved without further user input.

6. The payment bridge system of claim 1, wherein the service provider computer must be configured by an authorized individual in order to enable the service provider computer to execute the payment bridge.

7. The payment bridge system of claim 1, wherein the service provider comprises a health care service provider.

8. The payment bridge system of claim 7, wherein the health care service provider comprises a medical or dental service provider.

9. The payment bridge system of claim 1, wherein the payment bridge updates the first type of practice management software with information associated with an approved requested credit card transaction by updating relevant bookkeeping fields of the first type of practice management software.

10. A payment bridge method for a service provider, comprising:
    provide an application server that stores a plurality of unique configuration keys, wherein each unique configuration key comprises a set of computer readable instructions executable by a computer to emulate the commands required to communicate with a respective type of practice management software, wherein each respective type of practice management software comprises a respective set of computer readable instructions that are executable by a computer to provide business management functionality, including generating invoices and bookkeeping functionality;
    provide a service provider computer system located remote from the application server and in communication with the application server for receiving one or more unique configuration keys, wherein a first type of practice management software is installed on the service provider computer system and wherein the first type of practice management software comprises a set of computer readable instructions that are executable by the service provider computer system to provide business management functionality, including generating invoices and bookkeeping functionality; and
    install a payment bridge on the service provider computer system, wherein the payment bridge comprises a set of computer readable instructions executable by the service provider computer system to:
       receive credit card transaction information for a requested credit card transaction involving payment of an invoice generated by the first type of practice management software, wherein the credit card transaction information comprises credit card information and payment amount,
       transmit the credit card transaction information to a gateway provider of a credit card payment processor,
       receive a response from the gateway provider, and
       communicate with the first type of practice management software to update the first type of practice management software with information associated with the requested credit card transaction if the requested credit card transaction is approved, wherein the payment bridge communicates with the first type of practice management software using a unique configuration key for the first type of practice management software received from the application server.

11. The payment bridge method of claim 10, further comprising providing a credit card scanner in communication with the payment bridge for receiving credit card information from a credit card that is scanned by or inserted into the credit card scanner.

12. The payment bridge method of claim 11, wherein the payment bridge encrypts the credit card information received from the credit card scanner before transmitting the credit card information to the gateway provider.

13. The payment bridge method of claim 12, wherein neither the payment bridge and nor the service providers computer system store unencrypted or encrypted credit card information after it has been transmitted.

14. The payment bridge system of claim 10, wherein the payment bridge updates the first type of practice management software after the requested credit card transaction is approved without further user input.

15. The payment bridge system of claim 10, wherein the service provider computer must be configured by an authorized individual in order to enable the service provider computer to execute the payment bridge.

16. The payment bridge system of claim 10, wherein the service provider comprises a health care service provider.

17. The payment bridge system of claim 16, wherein the health care service provider comprises a medical or dental service provider.

18. The payment bridge system of claim 10, wherein the payment bridge updates the first type of practice management software with information associated with an approved requested credit card transaction by updating relevant bookkeeping fields of the first type of practice management software.

* * * * *